Figure 1:
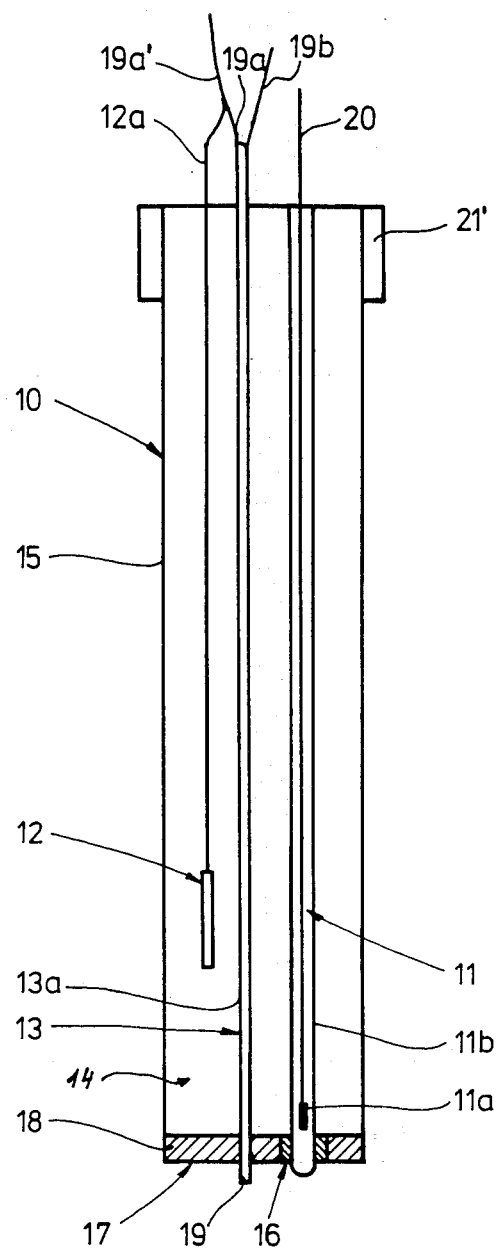

United States Patent [19]

Stellmacher

[11] Patent Number: 4,657,657
[45] Date of Patent: Apr. 14, 1987

[54] MULTIPLE COMBINATION ELECTRODE WITH ASSOCIATED MULTI-POINT PLUG MOUNT

[75] Inventor: Klaus Stellmacher, Calw, Fed. Rep. of Germany

[73] Assignee: Conducta Gesellschaft fur Mess-und Regeltechnik mbH & Co., Gerlingen, Fed. Rep. of Germany

[21] Appl. No.: 627,846

[22] Filed: Jul. 5, 1984

[30] Foreign Application Priority Data

Jul. 6, 1983 [DE] Fed. Rep. of Germany ....... 3324297

[51] Int. Cl.⁴ .............................................. G01N 27/46
[52] U.S. Cl. .................................... 204/400; 204/433; 204/435; 204/286; 204/297 R
[58] Field of Search ............... 204/400, 420, 435, 286, 204/297 R

[56] References Cited

U.S. PATENT DOCUMENTS

| 3,468,780 | 9/1969 | Fischer | 204/422 |
| 3,476,672 | 11/1969 | Snyder et al. | 204/286 |
| 3,498,899 | 3/1970 | Kater et al. | 204/420 |
| 3,784,459 | 1/1974 | Jackson | 204/423 |
| 3,785,947 | 1/1974 | Baldwin et al. | 204/422 |
| 4,018,661 | 4/1977 | Brushwyler | 204/420 |
| 4,162,211 | 7/1979 | Jerrold-Jones | 204/420 |
| 4,218,299 | 8/1980 | Lindell et al. | 204/420 |
| 4,233,143 | 11/1980 | Knudsen | 204/415 |
| 4,284,321 | 8/1981 | Detemple et al. | 204/420 |
| 4,311,151 | 1/1982 | Hagihara | 204/415 |
| 4,466,878 | 8/1984 | Di Nitto et al. | 204/415 |

Primary Examiner—T. Tung
Attorney, Agent, or Firm—McAulay, Fields, Fisher, Goldstein & Nissen

[57] ABSTRACT

A multiple combination electrode with associated multi-point plug mount, wherein the three measuring systems provided are arranged in a single electrode shaft provided on its one end with the measuring plane and carrying on its other end a plug-mount part forming, together with an associated matching plug-mount part fixing the connection cable, a triple plug unit with concentrically arranged plug contacts.

8 Claims, 3 Drawing Figures 4,657,657

1

MULTIPLE COMBINATION ELECTRODE WITH ASSOCIATED MULTI-POINT PLUG MOUNT

PRIOR ART

The present invention starts out from a multiple combination electrode with an associated multi-point plug mount of the species described in the preamble of the main claim. The use of combination electrodes, for example in electrode measurements working on the ion-selective principle, has been previously known; the combination of the pH electrode on the one hand with the reference electrode on the other hand in a common glass area forming the electrode shaft simplifies the measuring set-up, the line wire arrangement and eliminates of course the need to provide a separate space for installation of each individual electrode. There is a general need for a multiple combination electrode for carrying out different measurements in a common measuring solution, i.e. for example for the combination of a pH-sensitive measurement with a reference potential measurement and simultaneous temperature measurement. Multiple measurements of this type may be of advantage for oxidation reduction potential derivation, conductivity measurements, dissolved oxygen measurements, etc.

It is, therefore, the object of the present invention to provide a multiple combination electrode with an associated multi-point plug mount of a design ensuring perfect potential transmission in the plug area without resistances, while permitting at the same time integration, in particular of the three measuring systems proposed herein, in a single glass or plastic tube which then forms the multiple combination electrode.

ADVANTAGES OF THE INVENTION

According to the invention, this object is achieved by the characterizing features of the main claim. This solution offers the advantage that in the field of main application, namely pH-sensitive measurements with reference potential measurements, a temperature sensor can be integrated simultaneously in the electrode and all measured potentials are taken over by the triple plug mounted arranged at the end of the electrode shaft opposite the measuring systems, it being possible to unite two of the electric lines resulting from the measuring systems for transmission of a common reference potential so that the other two lines will carry potentials corresponding to the concentration or proportionate quantity of specific ions and a potential proprotional to the temperature.

Another advantage of the invention is to be seen in the fact that the temperature measurement is effected on the same measuring plane in which the sensor tip for determining the ion activity (or other possible types of measurement) is located. If the temperature measuring system is integrated into the multiple combination electrode, the temperature sensor consists advantageously of a thermistor pill, more generally a measuring resistor or thermocouple or specifically a so-called NTC resistor, whose NTC pill, which is sealed in a glass tip and arranged at the end of an inner protective tube passes through the electrode shaft, is located at the level of the sensor head performing, for example, the pH measurement.

It is another advantage of the invention that all the measuring systems and the connection to the plug mount are united in one electrode shaft according to DIN so that a universally applicable measuring systems is obtained which lends itself to a plurality of multiple measurements, for example in the field of pH-sensitive measurements with simultaneous determination of the reference potential and the temperature of the measuring solution, oxidation reduction potential derivation, conductance cell measurements, measurements of dissolved oxygen, and the like.

Finally, it is a further advantage of the invention that the particular arrangement of the multi-point plug mount at the end of the electrode shaft excludes any contact errors and that the triaxial arrangement of the contacts in the form of concentrically arranged contact rings with interposed insulations and a common plastic cover ensures that a perfect extensive contact area is provided for transmitting the individual potentials and perfect contact is established, the risk of tilting or erroneous connection in the area of the detachable plug mount being excluded through the special arrangement selected.

Other improvements of the invention are provided by the features of, and described in the sub-claims.

DRAWING

Figure 2A:
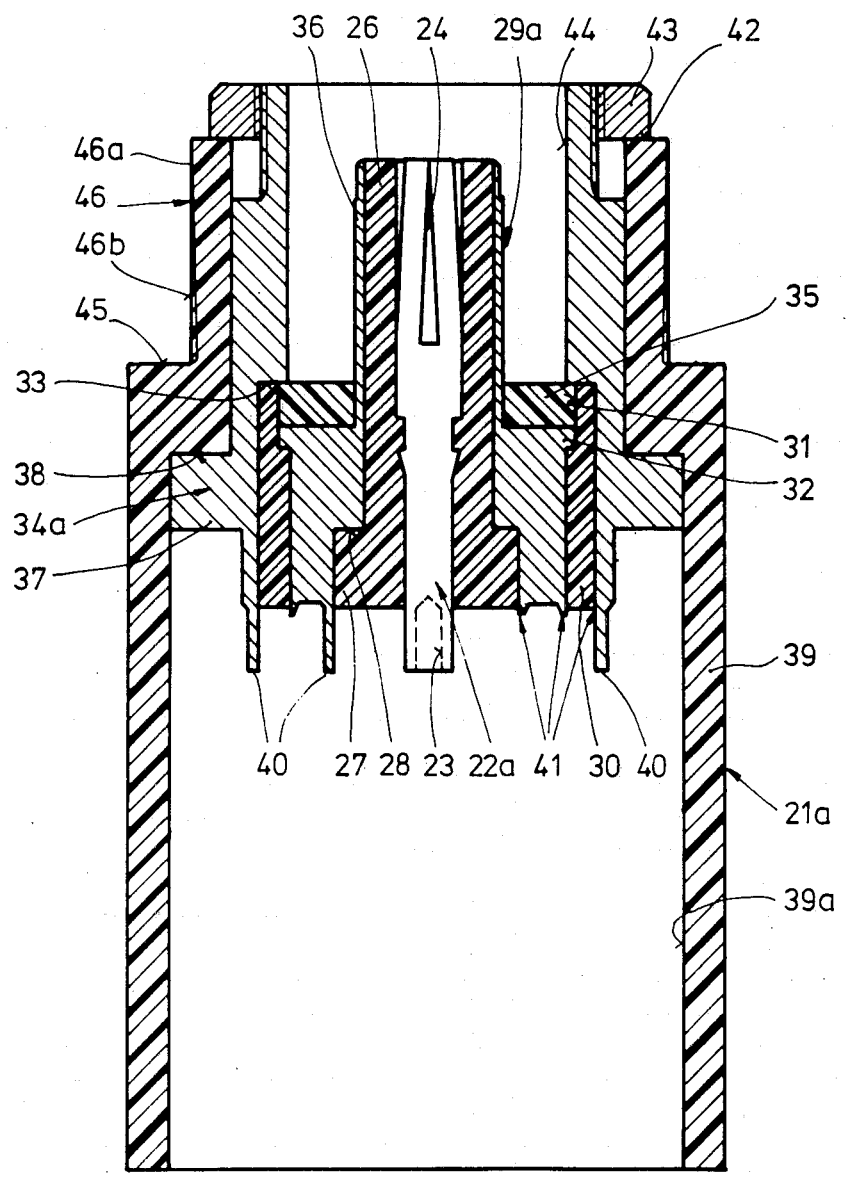
Figure 2B:
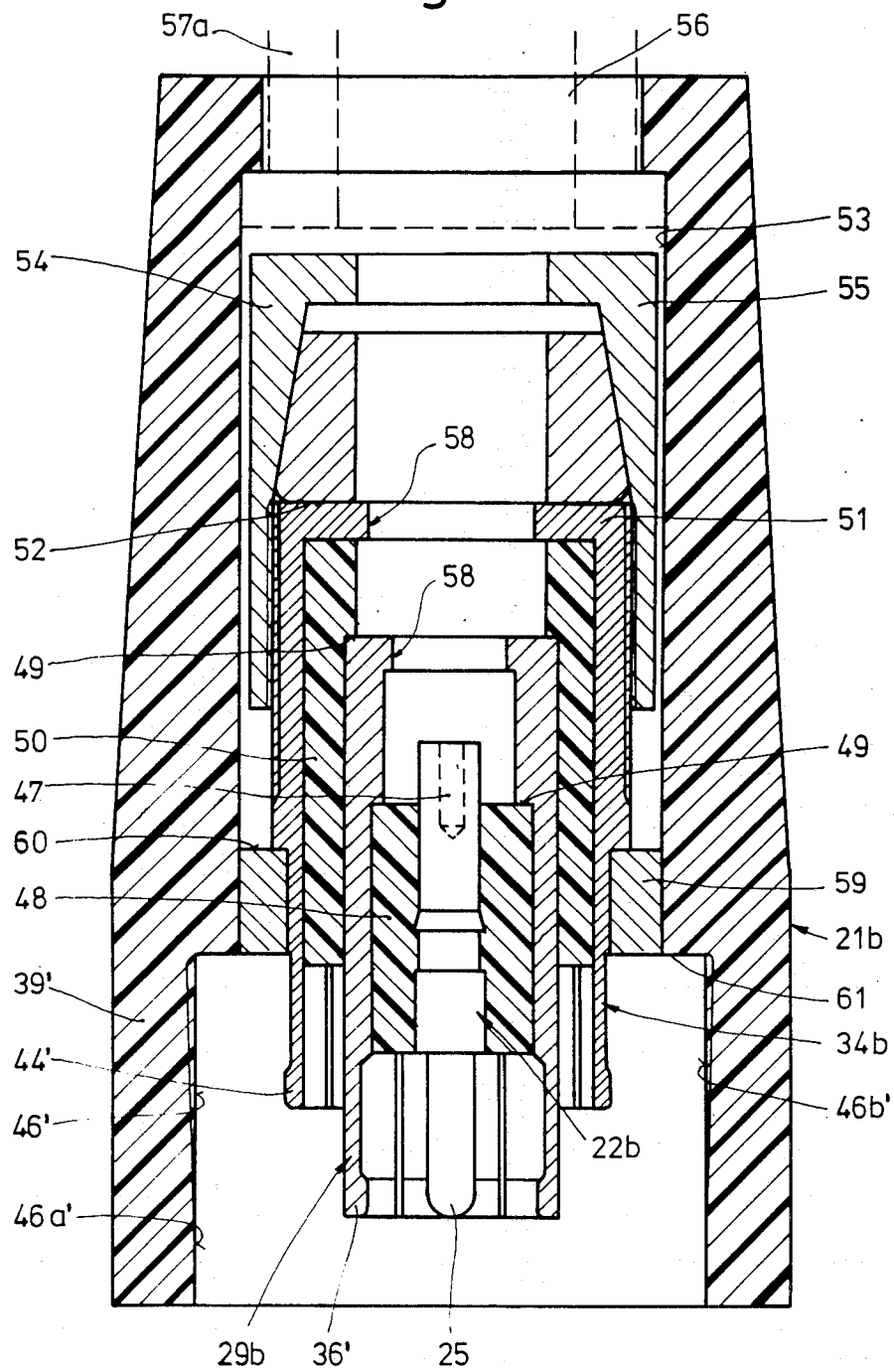

One embodiment of the invention is shown in the drawing and will be described in the following specification. In the drawing:

FIG. 1 shows a diagrammatic longitudinal cross-section through the multiple combination electrode of the invention, including the electrode shaft up to the transition to the multiple plug mount; and FIGS. 2a and 2b show longitudinal cross-sections through one embodiment of the detachable plug mount, with concentrically and coaxially arranged plug contacts.

DESCRIPTION OF EXAMPLES

The arrangement shown in FIG. 1 in connection with FIGS. 2a and 2b may be regarded as a triaxial electrode with triple-point plug mount, the three integrated measuring systems accommodated in the shaft 10 of the electrode being formed in the embodiment shown in the drawing by the measuring electrode portion 11, the reference portion 12 and, thirdly, a temperature sensor 3, as a preferred application. In a typical embodiment, the measuring electrode may consist of a galvanic half-cell, for instance a pH measuring electrode. The reference electrode portion may comprise a double transition—not being part of the invention and, therefore, not shown in the drawing—and dips into the form of a cartridge in the transition electrolyte 14 which fills the tube 15 of the electrode shaft 10.

It is an essential feature of the present invention that the reference transition between the transition electrolyte 14 and the measuring solution in which the multiple combination electrode is immersed, is formed by a diaphragm ring 16 surrounding the measuring electrode head symmetrically. The measuring electrode portion, together with the symmetrically arranged diaphragm ring 16 may then be provided in offset arrangement within the electrode shaft because the latter comprises still another glass or plastic tube 13a which passes through the electrode shaft right to the measuring plane 17 where the tube 13a projects through a sealing 18 so that its tip which carries the thermistor pill 19 dips directly into the measuring solution. The thermistor pill, i.e. the temperature-sensitive sensing element, consists preferably of an NTC resistor whose two line wires indicated by the reference numbers 19a and 19b are guided upwards through the transition electrolyte within the tube 13a; the line wire arriving from the reference cartridge 12 is indicated by 12a, while the precious metal wire of the measuring electrode portion is indicated by 20. As the measuring systems are all separate, it is possible without any problems to connect the one line wire, here 19a, of the temperature sensor system with the precious metal wire 12a of the reference electrode portion so that the ion activity can be measured at the connection wire 20, against the connection wire 19a carrying reference potential, while the temperature can be measured at the connection wire 19b, against the connection wire 19a' carrying reference potential.

The tube ends of the temperature sensor 13 and of the measuring electrode portion may be either sealed into the glass at the end of the electrode shaft or fastened in any other suitable manner, for instance by bonding or sealing with a suitable compound, such as epoxy resin, or the like. In FIG. 1, the end of the plug-mount holder of that part of the plug mount which is fixed to the electrode can just be seen at 21'. This first part of the plug mount is indicated in FIG. 2a generally by the reference number 21a, while the second plug-mount part connected with the cable is indicated by the reference number 21b and shown in FIG. 2b. The two plug-mount parts 21a, 21b are necessarily provided with complementary plug contacts which will be described hereafter using the same reference numbers for the matching parts, distinguished only by the additions a or b.

The first plug-mount part 21a fixed to the electrode shaft comprises, from the inside to the outside, a central inner plug socket 22a consisting of a suitable conductive material, such as brass or gold or corresponding alloys, forming the inner conductor. The plug socket 22a may have a solid central portion and is provided with a rear notch 23 serving as soldering pin for connection of one of the conductors 19a/12a, 19b or 20. The front portion of the inner conductor 22 is slotted, as indicated at 24, to form resilient tongues so that the contact is safely established when a central pin 25 of the inner conductor 22b of the other plug-mount part is introduced into the inner jack formed by the said resilient tongues.

The inner conductor 22a of the first plug-mount part 21a is surrounded by an insulator 26 of substantially cylindrical shape in which the inner conductor 22a may also be embedded or sealed. A rear projecting collar 27 of the inner insulator 26 bears against a shoulder 28 of the second substantially cylindrical (metallic) medium conductor 29a surrounding the inner insulator 26 and being likewise surrounded by a substantially cylindrical insulator 30 provided with a front-end annular recess 31 receiving an outwardly projecting annular flange 32 of the medium conductor 29a and, in addition, a front-end insulator ring 35 which is in this manner clamped against an inner shoulder 33 of the cylindrical outer conductor 34a. The forward cylindrical portion of the medium conductor 29a which projects in the direction of the second plug-mount part forms a pin 36 for being introduced into a corresponding matching jack 36' of the associated medium conductor 29b at the other plug-mount part which will be described further below.

The outer conductor 34a is provided with an annular projection 37 resting on a corresponding shoulder 38 of an outer plastic case 39 enclosing the whole contact system. The free rear bore 39a of the plastic case 39 is adapted to receive, for example, the shaft of the multiple combination electrode shown in FIG. 1. The connection to the respective line wires is effected by soldering lugs provided at the concentrical outer and medium conductors and indicated generally by 40. The individual cylindrical components which are already held in position by annular recesses and projections are further secured in place by projecting marginal portions provided at the medium and outer conductors and bent over as indicated at 41.

As the annular projection 37 of the outer conductor 34a rests against the shoulder 38, it appears that the concentrical insulator and contact parts can be securely held in the surrounding plastic case 39 by a (brass) nut 43 bearing against the front end face 42 of the plastic case. In the embodiment shown, the inner annular wall 44 of the outer conductor 34a, which is spaced a certain distance from the pin 36 of the medium conductor, forms a rigid jack for receiving a resilient inner pin 44' formed by the associated outer conductor 34b of the second plug-mount part 21b.

It is a further essential feature of the design of the plug mount according to the invention that one of the two parts—in the embodiment shown the first plug-mount part 21a fixed to the electrode shaft 10—is reduced in diameter in its front portion pointing towards the other plug-mount part to form a shoulder whereby a plug-in, fitting and threading portion 36 is formed which comprises at the forward end a plain surface 46a followed towards the rear by a threaded portion 46b. This design makes it possible to use the reduced fitting and threaded portion 46 of the first case part to fit the plain-walled front portion 46a initially concentrically in the likewise plain-walled inner bore 46a' of the surrounding plastic case 39' of the second plug-mount part so as to fit the two parts snugly into each other whereafter a screwed connection can be realized by screwing the outer thread 46b upon the inner thread 46b' of the bore 46' which likewise begins at some distance from the outer end of the bore. This is the moment when the respective plug contacts of the inner conductor, the medium conductor and the outer conductor engage each other, and full introduction will be achieved only when the two parts are screwed home fully. In this manner, any offsets and distorsions are prevented, and the contacts are safely established, the rotary movement serving on the one hand to lock the two plug-mount parts against each other so as to prevent any unwanted loosening and also to establish an extremely intimate and safe electric contact as the contacts will engage each other and slide upon each other during screwing so that they will form optimum metallized and oxide-free transitions.

The contacts of the plug-mount part also form together with the interposed insulator a concentrical cylindrical structure in which the individual parts are provided with stepped inner bores forming shoulders or outwardly projecting collars, as necessary, except for the inner conductor which is of a substantially solid design and which is indicated in FIG. 2b by the reference number 22b. The inner conductor, with its soldering point indicated at 47, is embedded in a surrounding cylindrical insulator 48 which is itself introduced into the inner bore of the medium conductor 29b and rests against a stop 49 formed by a shoulder. The medium conductor 29b in turn is fitted in a surrounding concentrical and cylindrical insulator 50 and rests on a shoulder 49, and the insulator 50 finally rests on a shoulder 52 formed by an inwardly projecting lower collar 51 of the cylindrical outer conductor 34b so that the whole number of concentrically arranged cylindrical conductors with interposed insulators are nested in each other and secured in place by stops. It goes without saying that the annular insulators 48 and 50 which are arranged between the inner conductor 22b and the medium conductor 29b, and between the medium conductor 29b and the outer conductor 34b, respectively, are set back relative to the respective plug contacts or pins of the other plug-mount part far enough to permit the cylindrical annular contacts to engage each other.

The outer conductor 34b is held at a distance relative to the surrounding inner bore 53 of the plastic case 39' of the second plug-mount part and is supplemented by a slotted clamping cone 54 fitted upon its lower annular end face and held in place by a screw cap 55. By tightening the screw cup upon an outer thread provided on the outer conductor 34b, the slotted cone 54 can be reduced in diameter so that a cable 56 whose bush is indicated by 57a can be fixed therein by clamping. The medium conductor and the outer conductor form soldering points indicated at 58 which may also be designed as lugs formed at the inwardly projecting annular shoulder. The whole structure is held by an intermediate nut 59 provided with an inner and an outer thread, screwed upon the outer conductor 34b down to a stop 60, and ending flush with the shoulder of the surrounding plastic case 39', as indicated at 61. The outer ends 36' of the medium conductor 29b, and 44' of the outer conductor 34b are longitudinally slotted to form resilient tongues, the jacket 36' formed by the medium conductor receiving the pin 36 of the other plug-mount part while the jacket 44' formed by the outer conductor is introduced into the jack 44 of the outer conductor 34a, with its resilient tongues bearing against the wall of the latter.

All features described and represented in the specification, the following claims and the drawing may be essential to the invention either individually or in any desired combination.

I claim:

1. A multiple combination electrode system for electro-analysis apparatus, comprising an elongated electrode shaft, three measuring systems within said electrode shaft having four wires for connection thereto, and a plug mount on the end of said shaft, the improvement comprising connecting means for connecting together two selected ones of said four wires to provide a three-wire system having a reference lead corresponding to the connected together wires which are adapted to receive reference potential thereon, and contact means including three corresponding concentric contact units within said plug mount; each of said concentric contact units connecting with a respective one of said three-wires to provide a unitary triple plug structure and insulating means between said concentriac contact units to insulate each one from the others, wherein the plug mount includes a first plug mount part connected to the electrode shaft and a second plug mount part connected to a cable, and wherein the contact means includes concentrical contact members separated by annular or cylindrical insulators in the first plug mount part and complementary contact members of matching shape and separated by annular or cylindrical insulators in the second plug mount part.

2. A multiple combination electrode in accordance with claim 1, characterised in that the first plug-mount part (21a) comprises a central inner conductor (22a) forming on its forward end a resilient contact jack (24), and a medium conductor (29a) surrounding the said inner conductor, separated therefrom by a cylindrical insulator (26) and including a supporting part forming a contact pin and a step and annular projection (28, 32) on the inside and outside, the said supporting part being surrounded on the one hand by an insulator (30) which is introduced into the cylindrical outer conductor (34a) down to a shoulder (33), a nut (43) retaining a collar (37) of the outer conductor (34a) in contact with a stop (38) formed by the plastic case (39).

3. A multiple combination electrode in accordance with claim 1, wherein a central contact member of the second plug mount part (21b) comprises a pin (25) and is surrounded by cylindrical insulator which is surrounded concentrically by a medium contact member (29b) forming at one end a jack (36'), the said medium contact member (29b) being surrounded in turn by a cylindrical insulator (50) and arranged in a stepped inner bore of the contact member concentrically therewith, the outer contact member (34b) forming at one end a hollow pin (44') for introduction into a jack (44) of the outer contact member at the first plug mount part (21a).

4. A multiple combination electrode in accordance with claim 1, wherein the contact members in the two plug mount parts are seated in central bores of surrounding plastic case parts (39, 39'), one of the case parts (39, 39') being provided with a guide shaft of reduced diameter projecting fowardly beyond the contact members, and the other case part forming a guiding and receiving bore (46') so that when the two plug mount parts (21a, 21b) are fitted together, the concentrical engagement of the two case parts fixes the contact members initially in concentrical alignment and therafter in firm engagement.

5. A multiple combination electrode in accordance with claim 4, wherein the two case parts have coacting projecting annular holders serving to fix the contact members in concentrical alignment at least over part of their lengths, with an inner or outer thread, respectively, so that the firm engagement of the contact members is achieved by screwing the two plug mount parts together.

6. A multiple combination electrode system in accordance with claim 1, characterized in that the three measuring systems include a measuring electrode portion (11), a reference electrode portion (12), and a temperature sensor (13), all of which are received within said electrode shaft (10).

7. A multiple combination electrode in accordance with claim 6, wherein the measuring electrode portion has a half-cell and the temperature sensor has an active part and wherein the half-cell (11a) of the measuring electrode portion is formed by a tube (11b) whose measuring tip passing beyond the electrode shaft (10) defines a measuring plane up to which the active part of the temperature sensor is guided by a separate tube (13a).

8. A multiple combination electrode in accordance with claim 7, further comprising a diaphragm ring (16) arranged symmetrically relative to the tip of the measuring electrode portion.

* * * * *